(12) United States Patent
Nakajima

(10) Patent No.: US 7,727,198 B2
(45) Date of Patent: Jun. 1, 2010

(54) INDWELLING NEEDLE ASSEMBLY

(75) Inventor: Hiroaki Nakajima, Narashino (JP)

(73) Assignee: Medikit Co. Ltd., Tokyo (JP)

( * ) Notice: Subject to any disclaimer, the term of this patent is extended or adjusted under 35 U.S.C. 154(b) by 437 days.

(21) Appl. No.: 11/604,894

(22) Filed: Nov. 28, 2006

(65) Prior Publication Data

US 2007/0185456 A1    Aug. 9, 2007

(30) Foreign Application Priority Data

Nov. 28, 2005    (JP) ............................ P2005-342584

(51) Int. Cl.
*A61M 5/178*    (2006.01)
(52) U.S. Cl. ............................ 604/164.01; 604/164.08; 604/164.12
(58) Field of Classification Search ............ 604/164.01, 604/164.08, 164.12, 198
See application file for complete search history.

(56) References Cited

U.S. PATENT DOCUMENTS

| | | | | |
|---|---|---|---|---|
| 4,747,831 A | * | 5/1988 | Kulli | 604/110 |
| 5,360,408 A | * | 11/1994 | Vaillancourt | 604/198 |
| 5,695,474 A | * | 12/1997 | Daugherty | 604/162 |
| 5,865,806 A | * | 2/1999 | Howell | 604/164.12 |
| 6,638,254 B2 | | 10/2003 | Nakagami | |
| 7,101,351 B2 | * | 9/2006 | Crawford et al. | 604/110 |
| 7,118,552 B2 | * | 10/2006 | Shaw et al. | 604/110 |
| 7,422,572 B2 | * | 9/2008 | Popov et al. | 604/198 |
| 2002/0156422 A1 | * | 10/2002 | Takagi et al. | 604/164.12 |
| 2004/0044313 A1 | * | 3/2004 | Nakajima | 604/167.02 |

FOREIGN PATENT DOCUMENTS

| | | |
|---|---|---|
| EP | 1 201 261 A | 5/2002 |
| EP | 1 374 942 A | 1/2004 |
| EP | 1 475 124 A | 11/2004 |

* cited by examiner

*Primary Examiner*—Nicholas D Lucchesi
*Assistant Examiner*—Ian K Holloway
(74) *Attorney, Agent, or Firm*—Smith Patent Office

(57) ABSTRACT

An indwelling needle assembly for introducing a catheter into a vascular system is disclosed. The indwelling needle assembly is provided with: a needle capable of being slidably fitted in the catheter and insertable into the vascular system; a base body fixed to a proximal end of the needle; a first sleeve slidably fitted around the base body, which is movable between a first position to expose a distal end of the needle and a second position to conceal the distal end of the needle; an elastic body intervening between the base body and the first sleeve so as to urge the first sleeve toward the second position; a second sleeve telescopically fitted to the first sleeve, which includes a latching device configured to hold the first sleeve at the second position; a cover fixed to the base body, which is so dimensioned as to house the first sleeve and the second sleeve when the first sleeve is at the first position; and a lock configured to releasably hold the first sleeve at the first position.

6 Claims, 3 Drawing Sheets

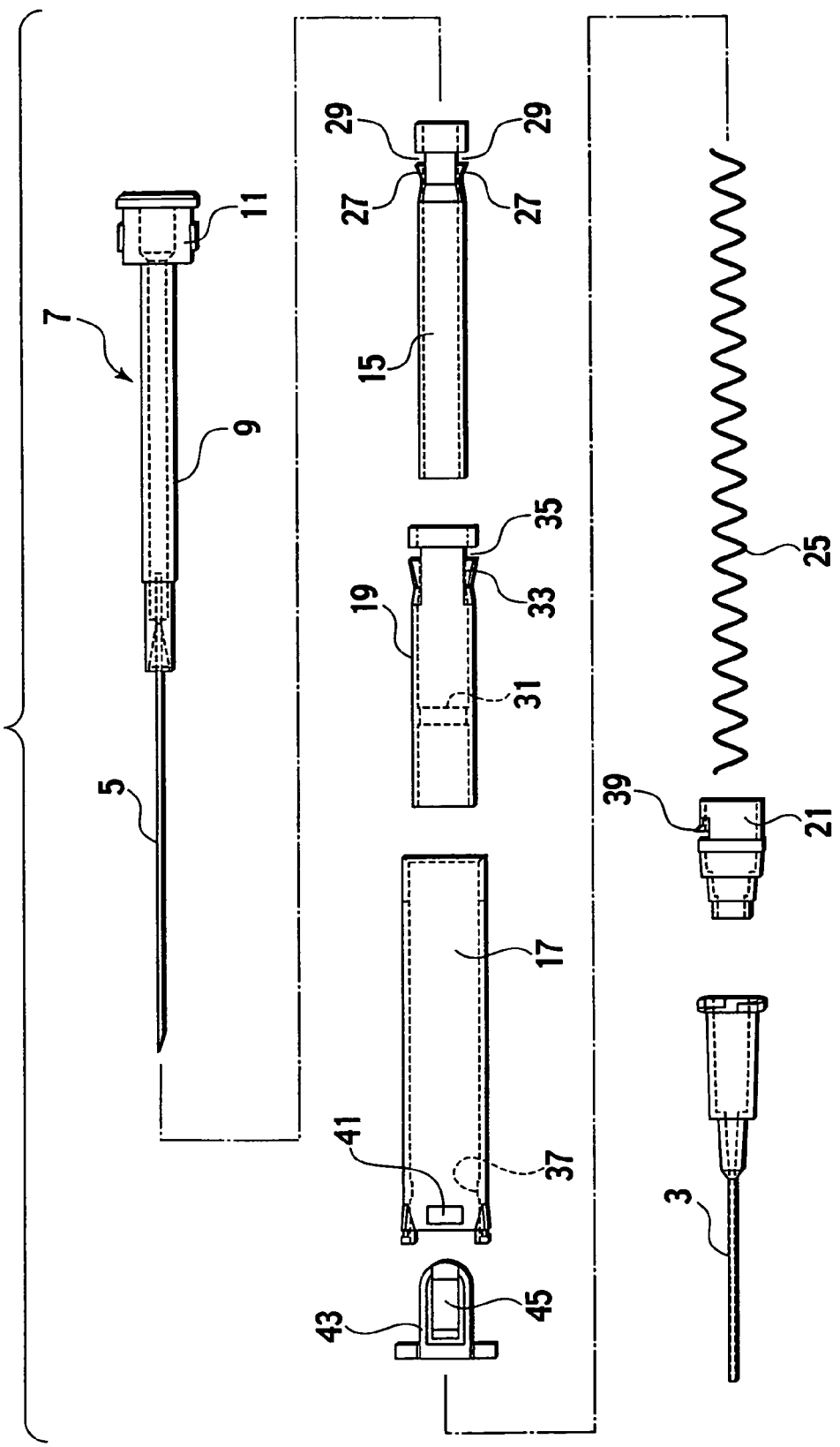

INDWELLING NEEDLE ASSEMBLY

BACKGROUND OF THE INVENTION

1. Field of the Invention

The present invention relates to an indwelling needle assembly used for introducing a catheter into a vascular system of a patient at a time of infusion.

2. Description of the Related Art

Catheters are used to infuse various medicinal fluids into vascular systems. To introduce such a catheter into a vascular system of a patient, a needle assembly with a needle fitted in the catheter is frequently used. After sticking the needle into the vascular system, the needle may be extracted but the catheter is left indwelled in the vascular system. When the needle is extracted, the needle must be safely covered so as to prevent accidental sticking. Some catheters are provided with telescopically extensible sleeves for covering the needles. However, extension of the sleeves by hands in itself may give rise to a risk of accidental sticking. An automatic extension mechanism may need a complex structure.

SUMMARY OF THE INVENTION

The present invention is intended for providing an indwelling needle assembly with a safety guard which is extensible by one-hand and has a relatively simple structure providing facility of assembly thereof.

According to an aspect of the invention, an indwelling needle assembly for introducing a catheter into a vascular system is provided with: a needle capable of being slidably fitted in the catheter and insertable into the vascular system; a base body fixed to a proximal end of the needle; a first sleeve slidably fitted around the base body, which is movable between a first position to expose a distal end of the needle and a second position to conceal the distal end of the needle; an elastic body intervening between the base body and the first sleeve so as to urge the first sleeve toward the second position; a second sleeve telescopically fitted to the first sleeve, which includes a latching device configured to hold the first sleeve at the second position; a cover fixed to the base body, which is so dimensioned as to house the first sleeve and the second sleeve when the first sleeve is at the first position; and a lock configured to releasably hold the first sleeve at the first position.

Preferably, the indwelling needle assembly is further provided with: a sleeve cap configured to receive repulsive force of the elastic body, which is fixed to a distal end of the first sleeve. More preferably, the lock is formed on the sleeve cap.

Still preferably, the indwelling needle assembly is further provided with: an operation piece configured to operate the lock to release the first sleeve from the first position, which is fixed to the cover to allow operation from an exterior of the cover.

Further still preferably, the indwelling needle assembly is further provided with: a catheter including a tube portion for being indwelled in the vascular system and so dimensioned as to fit along the needle, and an adapter portion for connecting an infusion device.

BRIEF DESCRIPTION OF THE DRAWINGS

FIG. 3 is an exploded plan view of the indwelling needle assembly.

DETAILED DESCRIPTION OF THE PREFERRED EMBODIMENT

An embodiment of the present invention will be described hereinafter with reference to FIGS. 1 to 3. Throughout the specification and claims, a relative term "distal" is defined and used as toward a needlepoint, and "proximal" is opposite thereto. In the appended drawings, distal and proximal directions are shown to the left and the right, respectively.

Figure 1:
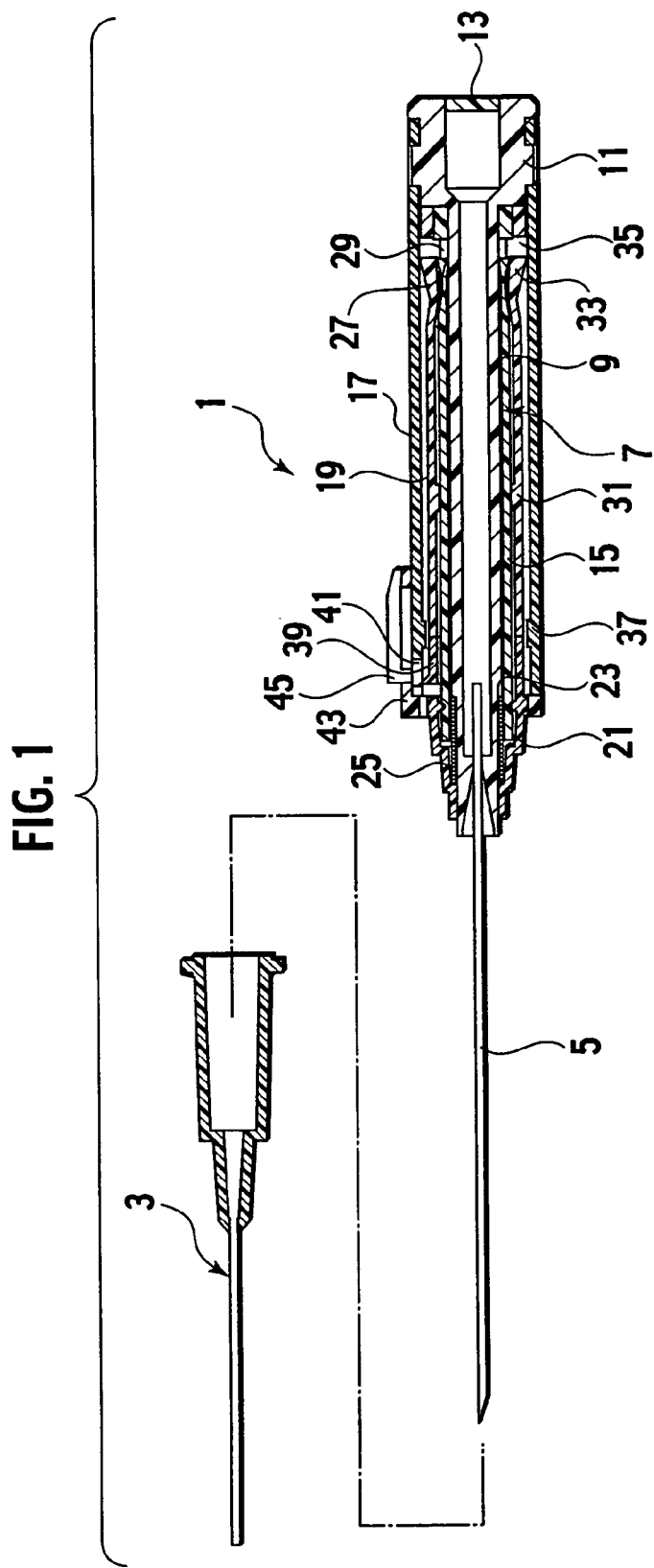
FIG. 1 is a partially exploded cross sectional view of an indwelling needle assembly in accordance with an embodiment of the present invention.
Figure 2:
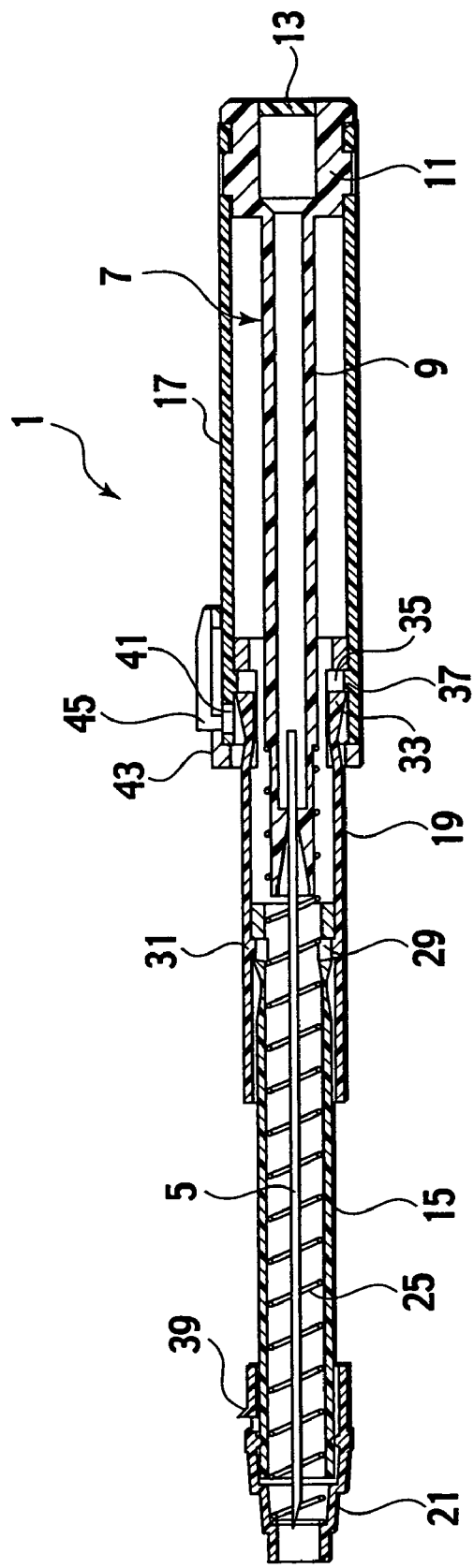
FIG. 2 is a cross sectional view of the indwelling needle assembly in a state that a first sleeve is projected to conceal a distal end of the needle.

Referring to FIG. 1, an indwelling needle assembly 1 according to the embodiment is provided with a catheter 3, a needle 5 capable of being fitted in the catheter 3, and a base body 7 fixed to a proximal end of the needle 5, sleeves 15 and 19, an elastic body 25 and a cover 17, all of which are coaxially engaged with each other.

The catheter 3 is provided with a tube portion for being indwelled in the vascular system and so dimensioned as to fit along the needle 5. The catheter 3 is further provided with an adapter portion formed at a proximal end thereof. The adapter portion is for fitting on the cover 17 and also for connecting any external infusion devices.

The base body 7 is a tubular body formed of a clear synthetic resin and is generally composed of a relatively thinner tubular portion 9 and a relatively thicker proximal portion 11 having engaging projections. The thinner tubular portion 9 has a further thinner neck near the distal end thereof and its boarder is made to be a stepped shoulder 23. A proximal end of the proximal portion 11 has an opening covered with a membrane 13 which allows permeation of gas but prevent permeation of liquid.

The first sleeve 15 is slidably fitted around the base body 7. Intervening between the first sleeve 15 and the cover 17, the second sleeve 19 is also slidably provided. Thereby the first and second sleeves 15, 19 are telescopically movable with respect to the needle 5, the base body 7 and the cover 17. The first sleeve 15 has an enough length to conceal a distal end (the needlepoint) of the needle 5 when the sleeves 15, 19 are fully extended. In contrast, when fully retracted, the sleeves 15, 19 are substantially fully housed in the cover 17 and the distal end of the needle 5 is exposed. Throughout the specification and the claims, a position of the first sleeve 15 in the fully retracted state is referred to as a first position and another position in the fully extended state is referred to as a second position.

Intervening between the base body 7 and the first sleeve 15, the elastic body 25 is provided so as to urge the first sleeve 15 toward the second position. When the first sleeve 15 is at the first position, the elastic body 25 is made compressed to have repulsive force. The elastic body 25 is preferably, but not limited to, a coil spring.

A sleeve cap 21 is fixed with a distal end of the first sleeve 15. The sleeve cap 21 is engaged with a distal end of the elastic body 25 so as to receive the repulsive force of the elastic body 25 and thereby urge the first sleeve 15 toward the second position.

Latching devices are provided for holding the first sleeve 15 at the second position when the sleeves 15 and 19 are telescopically extended. The first sleeve 15 is provided with a latching recess 29 with a ratchet tooth 27 on the exterior surface at the vicinity of the proximal end thereof. The second sleeve 19 is provided with a latching projection 31 on the internal surface thereof so as to latch on the latching recess 29 of the first sleeve 15. The second sleeve 19 is further provided with a latching recess 35 with a ratchet tooth 33 as similar to those of the first sleeve 15. Correspondingly, the cover 17 is provided with a latching projection 37 on the internal surface thereof so as to latch on the latching recess 35 of the second sleeve 19. Thereby, the first sleeve 15 is held at the second position when the sleeves 15 and 19 are telescopically extended.

In the course of movement of the first sleeve 15 from the first position to the second position, the latching projection 31 of the second sleeve 19 first moves toward the latching recess 29 with the ratchet tooth 27 of the first sleeve 15 and then goes over the ratchet tooth 27. Then the latching projection 31 latches on the latching recess 29 so that the second sleeve 19 moves integrally with the first sleeve 15. When the first sleeve 15 further moves toward the second position, the latching projection 37 of the cover 17 goes over the ratchet tooth 33 and latches on the latching recess 35 of the second sleeve 19. Then the first sleeve 15 and the second sleeve 19 come to be held in this state.

By means of the ratchet teeth 27 and 33, opposite movement of the sleeves 15 and 19, namely unlatching of the latching devices, is prevented. Thereby the latching devices irreversibly hold the first sleeve 15 at the second position as shown in FIG. 2, after once the first sleeve 15 is at the second position.

With respect to the latching devices described above, either elements should be projected or receded is of course relative and hence either will do.

The indwelling needle assembly 1 is further provided with a locking device for releasably holding the first sleeve 15 at the first position. The sleeve cap 21 fixed with the first sleeve 15 has an engaging projection 39 elastically projecting outward. Correspondingly, the cover 17 has an engaging opening 41. When the first sleeve 15 with the second sleeve 19 is retracted in the cover 17, the engaging projection 39 gets into and thereby engages with the engaging opening 41 so that the first sleeve 15 is held at the first position.

The indwelling needle assembly 1 is further provided with a lock releaser 43 for enabling release of the lock from the exterior of the cover 17. The lock releaser 43 is provided with an operation piece 45, which is an elastically deformable cantilever. The lock releaser 43 is so formed as to fit with the distal end of the cover 17 and the operation piece 45 is so dimensioned as to hang over the engaging opening 41. When an operator presses the operation piece 45 into the engaging opening 41, the operation piece 45 subsequently presses the engaging projection 39 to release engagement between the engaging projection 39 and the engaging opening 41. Thereby the first sleeve 15 is released from being held at the first position. Then the first sleeve 15 is given repulsive force from the elastic body 25 to move toward the second position and subsequently, as mentioned above, the second sleeve 19 moves integrally with the first sleeve 15. As a result, the sleeves 15 and 19 are telescopically extended and held at the second position.

As mentioned above, when once the sleeves 15 and 19 are telescopically extended by means of the repulsive force of the elastic body 25, the first sleeve 15 is irreversibly held at the second position to conceal the distal end of the needle 5. This state effectively prevents accidental sticking of the needle 5 to an operator or such. Further, movement of the first sleeve 15 from the first position to the second position is enabled merely by operation of the operation piece 45, which can be carried out merely by one-hand.

Referring to FIG. 3, assembly of the indwelling needle assembly 1 will be described hereinafter. First, the first sleeve 15 is inserted into the second sleeve 19 through the proximal end thereof to form a telescopic sleeve assembly. The lock releaser 43 is fitted with the distal end of the cover 17. Then the telescopic sleeve assembly is inserted into the cover 17 with the lock releaser 43 through the proximal end thereof.

Next, the base body 7 fixed with the needle 5 is inserted into the sleeve assembly with the cover 17 through the proximal end thereof. The proximal portion 11 of the base body 7 is pressed into the proximal end of the base body 7 so as to engage the engaging projections of the proximal portion 11 with the proximal end of the base body 7. Thereby the cover 17 and the proximal portion 11 with the sleeve assembly are integrated.

Next, the elastic body 25 such as a coil spring is inserted into the sleeve assembly through the distal end thereof. After the proximal end of the elastic body 25 abuts on the stepped shoulder 23 of the thinner tubular portion 9 of the base body 7, the sleeve cap 21 is engaged with the distal end of the elastic body 25. Then, by pressing the sleeve cap 21, the elastic body 25 is compressed, and finally the engaging projection 39 of the sleeve cap 21 is made engaged with the engaging opening 41 of the cover 17.

After the above procedures, by inserting the exposed needle 5 into the catheter 3, the assembly of the indwelling needle assembly 1 is completed. As the indwelling needle assembly 1, aside from the needle 5, is formed of a clear synthetic resin, the interior of the indwelling needle assembly 1 is visible from the exterior.

When an operator intends to introduce the catheter 3 into a vascular system of a patient, the needle 5 fitted in the catheter 3 is stuck into the patient's arm or such. When the distal end of the needle 5 reaches the patient's vascular system, blood flowing into the interior thereof is visible from the exterior, thereby the operator can confirm that insertion of the needle 5 is certainly achieved. After confirmation, the needle 5 is removed though the catheter 3 is left indwelled. The operator may press the operation piece 45 of the lock releaser 43 by his/her finger or such so as to extend the sleeves 15 and 19. As the distal end of the needle 5 is concealed with the first sleeve 15, the operator will safely dispose of the needle 5 without accidental sticking.

Although the invention has been described above by reference to a certain embodiment of the invention, the invention is not limited to the embodiments described above. Modifications and variations of the embodiment described above will occur to those skilled in the art, in light of the above teachings.

The contents of Japanese Patent Application No. 2005-342584 (filed Nov. 28, 2005) are incorporated herein by reference in its entirety.

What is claimed is:

1. An indwelling needle assembly for introducing a catheter into a vascular system, the indwelling needle assembly comprising:

a needle capable of being slidably fitted in the catheter and insertable into the vascular system;

a base body fixed to a proximal end of the needle;

a first sleeve slidably fitted around the base body, the first sleeve being movable between a first position to expose a distal end of the needle and a second position to conceal the distal end of the needle;

an elastic body intervening between the base body and the first sleeve so as to urge the first sleeve toward the second position;

a second sleeve telescopically fitted to the first sleeve, the second sleeve including a latching device configured to hold the first sleeve at the second position;

a cover fixed to the base body and slidably fitted to the second sleeve to allow the first sleeve and the second sleeve to be telescopically movable, the cover being so dimensioned as to house the first sleeve and the second sleeve when the first sleeve is at the first position; and a lock configured to releasably hold the first sleeve at the first position.

2. The indwelling needle assembly of claim 1, further comprising: a sleeve cap configured to receive repulsive force of the elastic body, the sleeve cap being fixed to a distal end of the first sleeve.

3. The indwelling needle assembly of claim 2, wherein the lock is formed on the sleeve cap.

4. The indwelling needle assembly of claim 1, further comprising: an operation piece configured to operate the lock to release the first sleeve from the first position, the operation piece being fixed to the cover to allow operation from an exterior of the cover.

5. The indwelling needle assembly of claim 1, further comprising: a catheter including a tube portion for being indwelled in the vascular system and so dimensioned as to fit along the needle, and an adapter portion for connecting an infusion device.

6. An indwelling needle assembly for introducing a catheter into a vascular system, the indwelling needle assembly comprising:

a needle capable of being slidably fitted in the catheter and insertable into the vascular system;

a base body fixed to a proximal end of the needle;

a first sleeve slidably fitted around the base body, the first sleeve being movable between a first position to expose a distal end of the needle and a second position to conceal the distal end of the needle;

an elastic body intervening between the base body and the first sleeve so as to urge the first sleeve toward the second position;

a second sleeve telescopically fitted to the first sleeve, the second sleeve including a latching device configured to hold the first sleeve at the second position;

a cover fixed to the base body, the cover being so dimensioned as to house the first sleeve and the second sleeve when the first sleeve is at the first position; and a lock configured to releasably hold the first sleeve at the first position;

wherein the second sleeve is provided to intervene between the first sleeve and the cover, the second sleeve is integrally movable with the first sleeve so that the first sleeve and the second sleeve are slidably movable with respect to the needle, the base body and the cover.

* * * * *